United States Patent
Deng (10) Patent No.: US 11,969,744 B2
(45) Date of Patent: Apr. 30, 2024

(54) STERILE SPRAY PUMP

(71) Applicant: SHENZHEN BONA PHARMA TECHNOLOGY CO., LTD., Guangdong (CN)

(72) Inventor: Yunhua Deng, Guangdong (CN)

(73) Assignee: SHENZHEN BONA PHARMA TECHNOLOGY CO., LTD., Guangdong (CN)

( * ) Notice: Subject to any disclaimer, the term of this patent is extended or adjusted under 35 U.S.C. 154(b) by 0 days.

(21) Appl. No.: 18/019,946

(22) PCT Filed: Nov. 8, 2019

(86) PCT No.: PCT/CN2019/116530
§ 371 (c)(1),
(2) Date: Jul. 25, 2023

(87) PCT Pub. No.: WO2020/103701
PCT Pub. Date: May 28, 2020

(65) Prior Publication Data
US 2024/0033760 A1   Feb. 1, 2024

(30) Foreign Application Priority Data

Nov. 19, 2018  (CN) .......................... 201811376534.9

(51) Int. Cl.
*B05B 11/10*   (2023.01)
*A61M 11/00*   (2006.01)

(52) U.S. Cl.
CPC ......... *B05B 11/1001* (2023.01); *A61M 11/00* (2013.01)

(58) Field of Classification Search
CPC ........................... B05B 11/1001; A61M 11/00
(Continued)

(56) References Cited

U.S. PATENT DOCUMENTS 7,780,042 B2 * 8/2010 Pruvot ............... B05B 11/1004
222/321.6
7,780,044 B2 * 8/2010 Leuliet ............... B05B 11/1074
222/321.9
(Continued)

FOREIGN PATENT DOCUMENTS

CN 202168992 U  3/2012
CN 102847627 A  1/2013
(Continued)

*Primary Examiner* — Lien M Ngo
(74) *Attorney, Agent, or Firm* — Global IP Services; Tianhua Gu (57) ABSTRACT

A sterile spray pump, including a main piston (30), a spray head (40), and a secondary piston (50) fixed inside the spray head (40) and mounted in a vertically movable manner on the main piston (30). A first compression space (10) and a second compression space (20) are formed between the secondary piston (50) and the main piston (30); a main liquid suction cavity (301) communicating with the inner cavity of a container and an air supply port (302) communicating with the main liquid suction cavity (301) are provided in the main piston (30); the air supply port (302) communicates with the second compression space (20), a filter element (601) is fixedly provided in the air supply port (302); the secondary piston (50) includes a secondary liquid suction cavity (501) communicating with the main liquid suction cavity (301), a first exhaust member (502), and a second exhaust member (503).

12 Claims, 6 Drawing Sheets

(58) Field of Classification Search
USPC ................. 222/321.1, 321.7, 321.8, 321.9
See application file for complete search history.

(56) References Cited

U.S. PATENT DOCUMENTS

| | | | | |
|---|---|---|---|---|
| 2007/0272713 A1* | 11/2007 | Le Maner | ........... | B05B 11/1074 222/321.9 |
| 2009/0140010 A1* | 6/2009 | Pruvot | ................ | B05B 11/1074 222/401 |
| 2012/0126035 A1* | 5/2012 | Greiner-Perth | ..... | B05B 11/1001 222/321.6 |
| 2013/0175303 A1* | 7/2013 | Donnette | ............ | B05B 11/1004 222/321.9 |
| 2017/0291183 A1* | 10/2017 | Lee | ..................... | B05B 11/1074 |

FOREIGN PATENT DOCUMENTS

| | | |
|---|---|---|
| CN | 205615927 U | 10/2016 |
| CN | 107539612 A | 1/2018 |
| CN | 109592203 A | 4/2019 |
| FR | 2714027 B1 | 3/1996 |
| JP | 2007253112 A | 10/2007 |

\* cited by examiner

STERILE SPRAY PUMP

CROSS REFERENCE TO RELATED PATENT APPLICATION

The present application is the US national stage of PCT/CN2019/116530 filed on 2019 Nov. 8, which claims the priority of the Chinese patent application No. 201811376534.9 filed on 2018 Nov. 19, which application is incorporated herein by reference.

TECHNICAL FIELD

The present disclosure relates to the field of storage of liquid (such as medicinal liquid, liquid cosmetics, liquid cleaning agents, etc.), in particular, to a sterile spray pump for spraying out liquid in a container.

BACKGROUND OF THE INVENTION

The spray pump is a pump that sprays liquid substances in an atomizing state when being pressed by a user. When the spray pump is used for spraying medicinal liquid, the spray pump usually has sterile requirements. At present, there are various types of spray pumps in the market, but all of them have the following shortcomings:

1. Conventional spray pumps mostly have an open spray head structure. After the spray pumps are used, the air directly contacts with the medicinal liquid at a spray head, and the medicinal liquid remains in the spray head. The residual medicinal liquid is easy to deteriorate after contacting with the air for a long time, and is sprayed out again in the next use, and thus, the use effect is directly affected.

2. Conventional spray pumps are designed with an air return structure, which is used for supplying external air into the container during the use of the spray pumps, otherwise the spray pumps cannot work normally, but the direct entry of external air into the container will pollute the medicinal liquid in the container.

3. Sterile spray pumps are mostly in the form of vacuum pumps, the loading capacity of medicinal liquid in a container provided with a vacuum pump shall not exceed 2/3 of the capacity of the container, and the capacity of the container is limited to some extent. If the capacity of the container is too large, the internal negative pressure is excessively high, which leads to unstable dosage; at the same time, with the increase of the times of use of the spray pump, the pressure inside the container increases continuously, which leads to the gradual reduction of the spray dose of the spray pump, thereby leading to the failure to use up all the liquid in the container.

SUMMARY OF THE INVENTION

The present disclosure provides a sterile spray pump. When the spray pump works normally, external air can be supplied into a container, and the capacity of the container, the loading capacity of medicinal liquid in the container, and the spray dose of the spray pump are not limited.

The sterile spray pump includes a main piston configured to be connected to a container, a spray head mounted in a vertically movable manner on the main piston, and a secondary piston fixed inside the spray head, where the secondary piston is mounted in a vertically movable manner on the main piston, and a first compression space and a second compression space are formed between the secondary piston and the main piston; a main liquid suction cavity communicating with the inner cavity of the container and an air supply port communicating with the main liquid suction cavity are provided in the main piston; the air supply port communicates with the second compression space, and a filter element covering the air supply port is fixedly provided in the air supply port; the secondary piston includes a secondary liquid suction cavity communicating with the main liquid suction cavity, a first exhaust member, and a second exhaust member; when the spray head is not pressed down, the space between the main piston and the secondary piston is sealed; after the spray head is pressed down and the main piston abuts against the first exhaust member and the second exhaust member, the first compression space communicates with the main liquid suction cavity through the first exhaust member, and the second compression space communicates with the exterior of the sterile spray pump through the second exhaust member.

Further, a filter connector provided in the main liquid suction cavity is fixed in the main piston; the air supply port is provided in the filter connector; and the filter element is a filter membrane fixed to the filter connector.

Further, the main piston includes a main inner ring portion and a main outer ring portion located at the outer peripheral side of the main inner ring portion; the secondary piston includes a secondary inner ring portion and a secondary outer ring portion located at the outer peripheral side of the secondary inner ring portion; the upper end of the main inner ring portion extends between the secondary outer ring portion and the secondary inner ring portion, and the first compression space is formed between the main inner ring portion, the secondary outer ring portion and the secondary inner ring portion; and the lower end of the secondary outer ring portion extends between the main inner ring portion and the main outer ring portion, and the second compression space is formed between the secondary outer ring portion, the main inner ring portion and the main outer ring portion.

Further, the main piston includes a first sealing ring at the upper end of the main inner ring portion and a second sealing ring at the upper end of the main outer ring portion, the first sealing ring is in sealing connection with the outer peripheral surface of the secondary inner ring portion, and the second sealing ring is in sealing connection with the outer peripheral surface of the secondary outer ring portion; the first exhaust member comprises at least two first convex ribs fixedly provided on the inner peripheral surface of the secondary inner ring portion and arranged in the circumferential direction of the secondary inner ring portion, and a first exhaust channel formed between two adjacent first convex ribs; the second exhaust member comprises at least two second convex ribs fixedly provided on the outer peripheral surface of the secondary outer ring portion and arranged in the circumferential direction of the secondary outer ring portion, and a second exhaust channel formed between two adjacent second convex ribs; and after the spray head is pressed down, the first convex ribs push the first sealing ring open to make the first compression space communicate with the main liquid suction cavity through the first exhaust channel, and the second convex ribs push the second sealing ring to make the second compression space communicate with the exterior of the sterile spray pump through the second exhaust channel.

Further, the sterile spray pump further includes a first return spring sleeved on the outer peripheries of the main outer ring portion and the secondary outer ring portion, and the upper and lower ends of the first return spring respectively abut against the secondary piston and the main piston.

Further, an air channel is formed between the main piston and the spray head; the outer periphery of the main piston is provided with a ring of upper clamping portion protruding outwards in a radial direction, and the inner periphery of the spray head is provided with a ring of lower clamping portion protruding inwards in a radial direction; when the spray head is not pressed down, the upper clamping portion abuts against the lower clamping portion, and the space between the lower clamping portion and the main piston is sealed; after the spray head is pressed down, the upper clamping portion is separated from the lower clamping portion, and the seal between the lower clamping portion and the main piston is released; and one end of the air channel communicates with the exterior of the sterile spray pump, and the other end communicates with the second compression space through the second exhaust member.

Further, the sterile spray pump further includes a spray nozzle fixed in the spray head, a sealing valve mounted between the spray nozzle and the secondary piston in a vertically movable manner, and a one-way valve assembly disposed at the upper end of the secondary liquid suction cavity; the spray head includes a spray port, a spray channel is formed between the secondary piston, and the spray head, the sealing valve and the spray nozzle; the one-way valve assembly is configured to communicate the spray channel with the secondary liquid suction cavity or block the spray channel from the secondary liquid suction cavity; when the spray channel is not filled with liquid, the space between the spray nozzle, the spray head and the sealing valve is sealed to block the spray channel from the spray port; and when the spray channel is filled with liquid, the sealing valve moves downward to make the spray channel communicate with the spray port.

Further, the sealing valve includes a lower valve section portion extending into the secondary piston, a second return spring is sleeved on the outer periphery of the lower valve section portion, and the upper and lower ends of the second return spring respectively abut against the sealing valve and the secondary piston.

Further, the sealing valve includes an upper valve section portion extending into the spray nozzle; and when the spray channel is not filled with liquid, the upper valve section portion is circumferentially sealed to the spray nozzle, the spray nozzle is circumferentially sealed to the spray head, and the spray head is end-face sealed to the sealing valve.

Further, the sealing valve includes a section of pushing surface located below the sealing joint of the sealing valve and the spray nozzle, and the pushing surface is a conical surface with an outer end obliquely extending outwards and downwards.

Further, the one-way valve assembly comprises a valve port opened on the secondary piston, a valve seat sealing surface provided at the inner side of the valve port and on the secondary piston, and a valve core mounted in the secondary piston in a vertically movable manner, and the valve port communicates with the spray channel; when the secondary liquid suction cavity is not filled with liquid, the valve core is in sealing connection with the valve seat sealing surface, and the valve core blocks the valve port from the secondary liquid suction cavity; when the secondary liquid suction cavity is filled with liquid, the valve core moves upwards, and the valve port communicates with the secondary liquid suction cavity.

Further, the valve seat sealing surface is a conical surface with the inner end obliquely extending inwards and downwards, and the valve core is a stainless steel ball.

To sum up, the sterile spray pump provided by the present disclosure has the following beneficial effects.

In the present application, the normal operation of the sterile spray pump is realized through the first compression space, the second compression space, the first exhaust member, the second exhaust member, and the air supply port, so that the sterile spray pump can suck the liquid in the container and spray out the liquid. As the sterile spray pump can normally supply external air into the container instead of using a vacuum pump, the sterile spray pump in the present application is not affected by the loading capacity and the number of times of use, and the capacity of the container, the loading capacity of medicinal liquid in the container and the spray dose of the spray pump are not limited. Moreover, the air exchange for the normal operation of the sterile spray pump is met through the filter element, the pollution is also avoided, and thus, the sterile requirement is achieved.

LIST OF REFERENCE NUMERALS

10 First compression space
20 Second compression space
30 Main piston
301 Main liquid suction cavity
302 Air supply port
303 Main inner ring portion
304 Main outer ring portion
305 First sealing ring
306 Second sealing ring
307 Upper clamping portion
308 First connecting portion
309 First step portion
310 Fifth connecting portion
311 Piston main body portion
312 Sixth connecting portion
313 Piston connecting portion
314 First cavity
315 Third step portion
40 Spray head
401 Lower clamping portion
402 Spray port
403 Fourth connecting portion
404 Spray head inner ring portion
405 Spray head outer ring portion
406 Second cavity
407 Seventh connecting portion
408 Fourth sealing surface
409 Sixth sealing surface
50 Secondary piston 501 Secondary liquid suction cavity
502 First exhaust member
503 Second exhaust member
504 Secondary inner ring portion
505 Secondary outer ring portion
506 Second connecting portion
507 Third connecting portion
508 First clamping groove
509 Fourth step portion
60 Filter connector
601 Filter element
602 Connector inner cavity
603 Pressing sleeve
604 Second step portion
70 Spray nozzle
701 Eighth connecting portion
702 Second clamping groove
703 Second sealing surface
704 Third sealing surface
80 Sealing valve
801 Lower valve section portion
802 Upper valve section portion
803 Pushing surface
804 Valve connecting portion
805 Valve outer ring portion
806 First sealing surface
807 Fifth sealing surface
90 One-way valve assembly
901 Valve port
902 Valve seat sealing surface
903 Valve core
110 Liquid suction pipe
120 First return spring
130 Air channel
140 Spray channel
150 Second return spring

DETAILED DESCRIPTION

The embodiments of the present disclosure will be described below through exemplary embodiments. Those skilled in the art can easily understand other advantages and effects of the present disclosure according to contents disclosed by the specification.

It is to be understood that the structures, the proportions, the sizes, and the like as drawn in the drawings of the specification are only used to corporate with the disclosure of the specification in order to facilitate the understanding and reading of those skilled in the art, and are not intended to limit the conditions under which the present disclosure can be implemented, and thus are not technically meaningful. Any modification of the structure, change of the proportional relationship or adjustment of the size should fall within the scope of the technical content disclosed by the present disclosure without affecting the obtainable effects and the achievable purposes of the present disclosure. At the same time, the terms such as "upper", "lower", "left", "right", "middle" and "one" as used in the specification are only for convenience of description and are not intended to limit the implementation scope of the present disclosure, and the change or adjustment of the relative relationship is also considered to be within the implementation scope of the present disclosure under the condition of no substantial change to the technical contents.

For the convenience of description, the vertical direction in the following embodiments is defined as follows: one end connected to the container in the sterile spray pump is defined as a lower end, the other end provided with a spray port 402 in the sterile spray pump is defined as an upper end, and the vertical direction is simultaneously the axial direction of the sterile spray pump.

Figure 1:
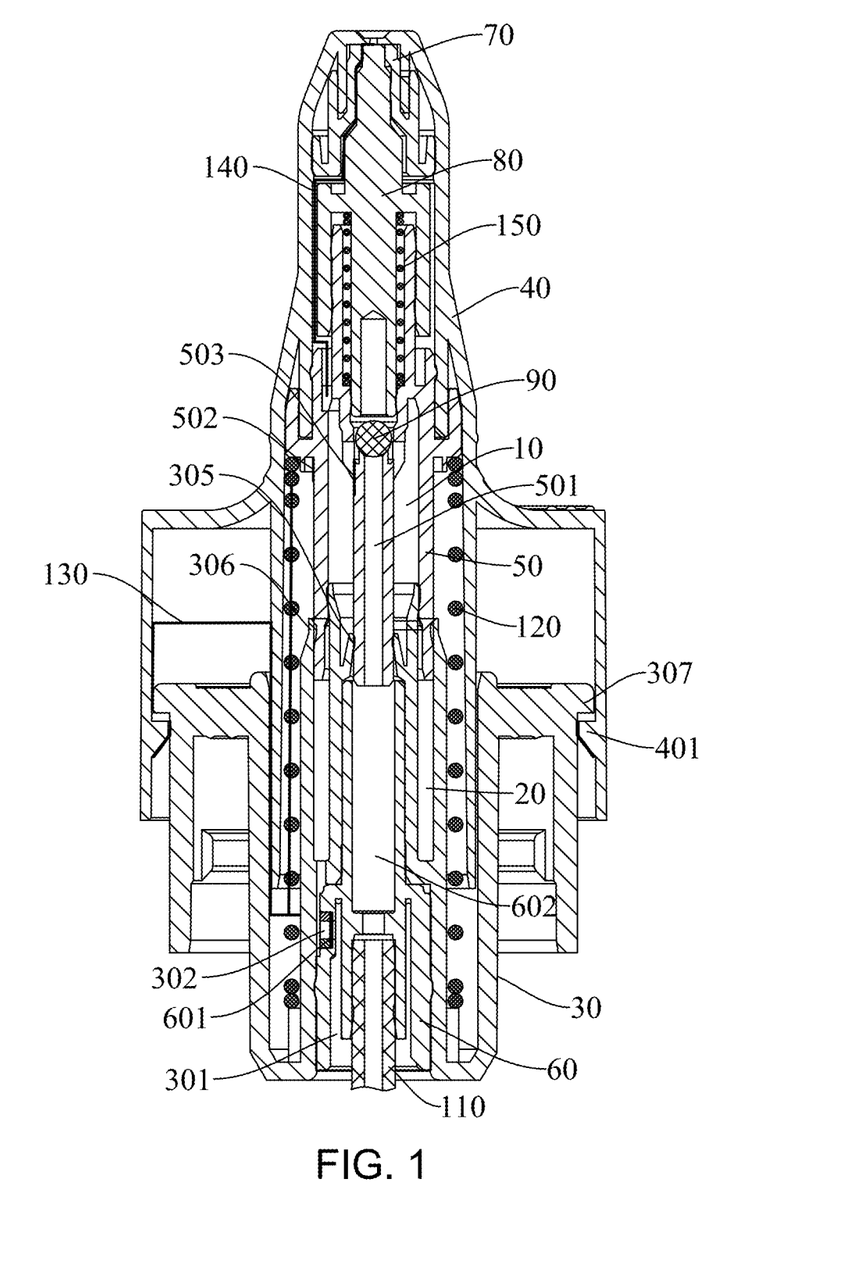
FIGS. 1 to 3 are schematic structural diagrams of a sterile spray pump in different states according to an embodiment of the present disclosure.
Figure 2:
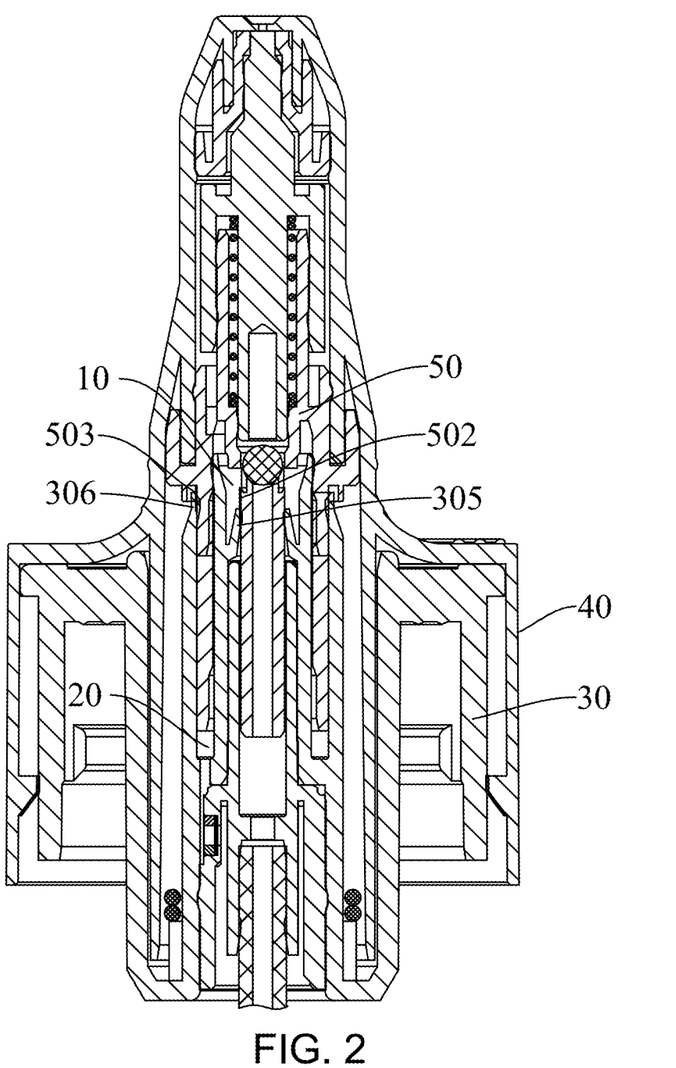
Figure 3:
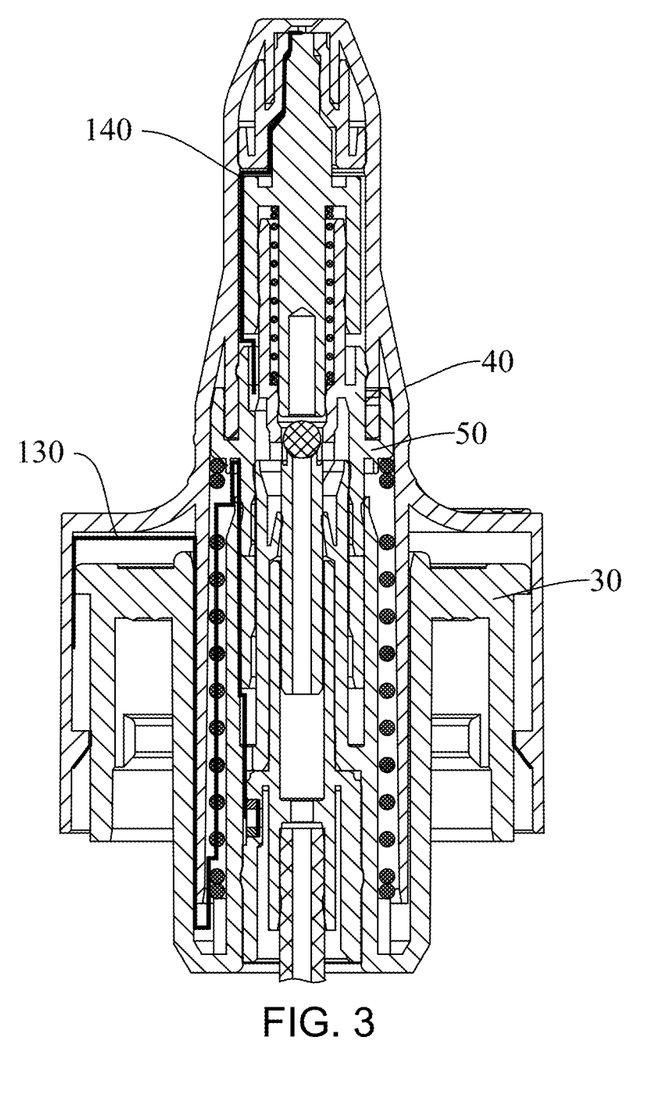

As shown in FIGS. 1, and 4 to 6, the sterile spray pump provided by this application includes a main piston 30, a spray head 40 and a secondary piston 50. The lower end of the main piston 30 is connected to a container, a main liquid suction cavity 301 extending up and down and an air supply port 302 extending radially are provided in the main piston 30. The lower end of the main liquid suction cavity 301 communicates with the inner cavity of the container, and the inner end of the air supply port 302 communicates with the main liquid suction cavity 301; the lower section portion of the spray head 40 is mounted on the outer periphery of the main piston 30 in a vertically movable manner; the upper end of the secondary piston 50 is fixed in the upper section portion of the spray head 40, and the secondary piston 50 moves vertically together with the spray head 40, and therefore, the lower end of the secondary piston 50 is mounted on the upper end of the main piston 30 in a vertically movable manner; the secondary piston 50 includes a secondary liquid suction cavity 501, a first exhaust member 502, and a second exhaust member 503; the secondary liquid suction cavity 501 extends vertically, and the lower end of the secondary liquid suction cavity 501 communicates with the upper end of the main liquid suction cavity 301; a first compression space 10 and a second compression space 20 are formed between the secondary piston 50 and the main piston 30; the lower end of the second compression space 20 communicates with the outer end of the air supply port 302; and a filter element 601 covering the air supply port 302 is fixedly provided in the air supply port 302. When the spray head 40 is not pressed down, as shown in FIG. 1, the space between the main piston 30 and the secondary piston 50 is sealed, so that the first compression space 10 does not communicate with the main liquid suction cavity 301, and the second compression space 20 also does not communicate with the exterior of the sterile spray pump. When the spray head 40 is pressed down to the lowest end, as shown in FIG. 2, the spray head 40 drives the secondary piston 50 to move down together relative to the main piston 30, so that the main piston 30 abuts against the first exhaust member 502 and the second exhaust member 503 of the secondary piston 50 at the same time, in the meanwhile, the first compression space 10 communicates with the main liquid suction cavity 301 through the first exhaust member 502, and the second compression space 20 communicates with the exterior of the sterile spray pump through the second exhaust member 503. Therefore, when the spray head 40 is pressed down to the lowest end for the first time, the compressed air in the first compression space 10 is discharged into the container after passing through the first exhaust member 502 and the main air suction cavity 301 in sequence, at the same time, the inner cavity of the container communicates with the exterior of the sterile spray pump through the main liquid suction cavity 301, the air supply port 302, and the second exhaust member 503 in sequence, and the compressed air in the container is discharged into the exterior after passing through the main liquid suction cavity 301, the air supply port 302 and the second exhaust member 503 in sequence, so that the pressure in the container is balanced with the external pressure; and when the spray head 40 is released, the spray head 40 drives the secondary piston 50 to rebound upwards, as shown in FIG. 3, negative pressure is formed in the first compression space 10, the second compression space 20, and the main liquid suction cavity 301, so that the liquid in the container is sucked out. When the spray head 40 is pressed down to the lowest end for the second time and the spray head 40 is pressed down to the lowest end every subsequent time, the first exhaust member 502 and the second exhaust member 503 make the pressure in the container be balanced with the external pressure, and the external air is supplied into the container after passing through the second exhaust member 503, the second compression space 20, the air supply port 302 and the main liquid suction cavity 301 in sequence. After that, the spray head 40 is released, so that the liquid in the container is sucked out. The processes are repeated until the liquid is sprayed out from the spray port 402 at the upper end of the spray head 40. Therefore, in the present application, the normal operation of the sterile spray pump is realized through the first compression space 10, the second compression space 20, the first exhaust member 502, the second exhaust member 503 and the air supply port 302, so that the sterile spray pump can suck the liquid in the container and spray out the liquid. As the sterile spray pump can normally supply external air into the container instead of using a vacuum pump, the sterile spray pump in this application is not affected by the loading capacity and the number of times of use, and the capacity of the container, the loading capacity of medicinal liquid in the container and the spray dose of the spray pump are not limited. Moreover, the air exchange for the normal operation of the sterile spray pump is met through the filter element 601, the pollution is avoided, and thus, the sterile requirement is achieved.

Figure 4:
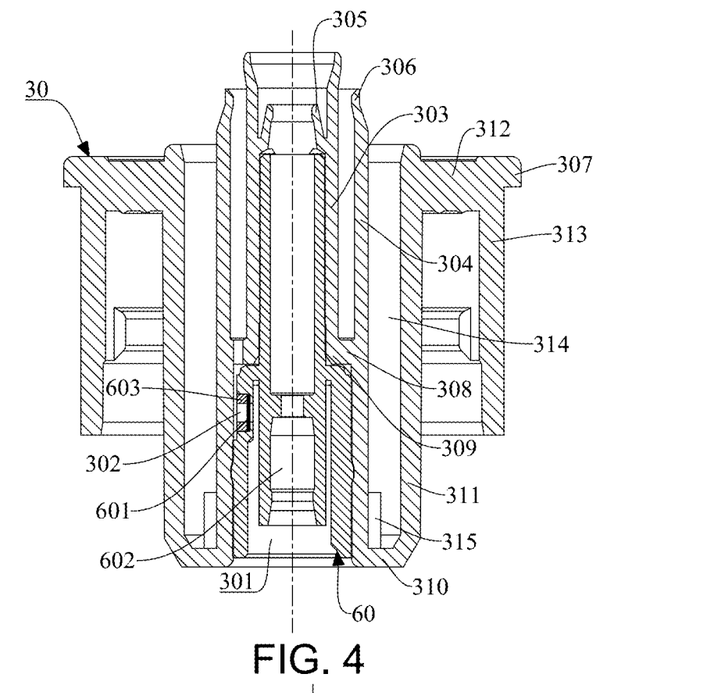
FIG. 4 is a schematic structural diagram of a main piston and a filter connector according to an embodiment of the present disclosure.

Further, the preferred connection structures between the main piston 30 and the container, and between the main piston 30 and the air supply port 302 are as follows: as shown in FIG. 1 and FIG. 4, a filter connector 60 provided in the main liquid suction cavity 301 is fixed in the main piston 30, the air supply port 302 is provided in the filter connector 60, and the filter element 601 is a filter membrane fixed to the filter connector 60; and the filter membrane allows air to get in and does not allow water to get in to prevent external pollutants from entering the interior of the container when external air is supplied to the container. In addition, the filter connector 60 includes a connector inner cavity 602. The connector inner cavity 602 is a portion of the main liquid suction cavity 301. The lower end of the filter connector 60 is fixedly connected to a liquid suction tube 110 in a tight fit. The upper end of the liquid suction tube 110 communicates with the connector inner cavity 602, and the lower end of the liquid suction tube extends into the liquid in the container. A portion of the secondary piston 50 passes through the connector inner cavity 602 of the filter connector 60 in a vertically movable manner. In addition, the filter membrane is fixed in a pressing sleeve 603. The pressing sleeve 603 is fixed in the air supply port 302, and thus, the filter membrane is fixedly provided in the air supply port 302.

Figure 5:
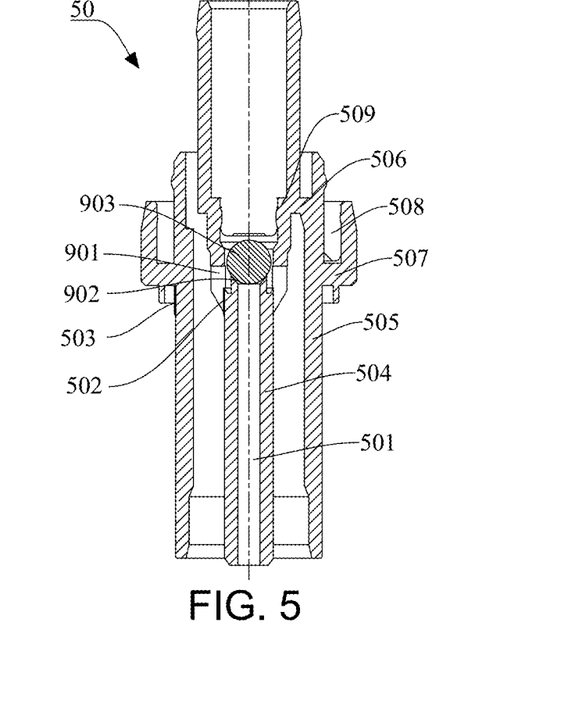
FIG. 5 is a schematic structural diagram of a secondary piston and a one-way valve assembly according to an embodiment of the present disclosure.

Further, the preferred connection structure between the main piston 30 and the secondary piston 50 is as follows: as shown in FIGS. 1, 4 and 5, the main piston 30 includes a main inner ring portion 303 extending vertically and a main outer ring portion 304 located at the outer peripheral side of the main inner ring portion 303 and extending vertically; the main inner ring portion 303 is connected to the main outer ring portion 304 through a first connecting portion 308 extending horizontally; the secondary piston 50 includes a secondary inner ring portion 504 extending vertically and a secondary outer ring portion 505 located at the outer peripheral side of the secondary inner ring portion 504 and extending vertically; the secondary inner ring portion 504 is connected to the secondary outer ring portion 505 through a second connecting portion 506 extending horizontally; the upper end of the main inner ring portion 303 extends between the secondary outer ring portion 505 and the secondary inner ring portion 504, and the first compression space 10 is formed between the main inner ring portion 303, the secondary outer ring portion 505 and the secondary inner ring portion 504; the lower end of the secondary outer ring portion 505 extends between the main inner ring portion 303 and the main outer ring portion 304, and the second compression space 20 is formed between the secondary outer ring portion 505, the main inner ring portion 303 and the main outer ring portion 304; and therefore, the first compression space 10 and the second compression space 20 are both annular cavities. In addition, the main piston 30 is formed with a first step portion 309 at the joint of the main inner ring portion 303, the main outer ring portion 304 and the first connecting portion 308, the first step portion 309 abuts against a second step portion 604 on the outer periphery of the filter connector 60, and thus, a limit is formed when the filter connector 60 is mounted in the main piston 30 upwards.

Further, as shown in FIGS. 1, 4 and 5, the main piston 30 includes a first sealing ring 305 at the upper end of the main inner ring portion 303 and a second sealing ring 306 at the upper end of the main outer ring portion 304, the first sealing ring 305 is in sealing connection with the outer peripheral surface of the secondary inner ring portion 504, and the second sealing ring 306 is in sealing connection with the outer peripheral surface of the secondary outer ring portion 505; the first exhaust member 502 includes two first convex ribs fixedly provided on the outer peripheral surface of the secondary inner ring portion 504 and arranged in the circumferential direction of the secondary inner ring portion 504, and a first exhaust channel formed between two adjacent first convex ribs; the second exhaust member 503 includes two second convex ribs fixedly provided on the outer peripheral surface of the secondary outer ring portion 505 and arranged in the circumferential direction of the secondary outer ring portion 505, and a second exhaust channel formed between two adjacent second convex ribs. When the spray head 40 is not pressed down, as shown in FIG. 1, the first sealing ring 305 is far away from the first convex ribs, so that the space between the main inner ring portion 303 of the main piston 30 and the secondary inner ring portion 504 of the secondary piston 50 is sealed, and then the first compression space 10 is blocked from the connector inner cavity 602 of the filter connector 60, that is, the first compression space 10 is blocked from the main liquid suction cavity 301, and then the first compression space 10 does not communicate with the interior of the container; at the same time, the second sealing cavity is far away from the second convex ribs, so that the space between the main outer ring portion 304 of the main piston 30 and the secondary outer ring portion 505 of the secondary piston 50 is sealed, and then the second compression space 20 is blocked from the outside. When the spray head 40 is pressed down to the lowest end, as shown in FIG. 2, the spray head 40 drives the secondary piston 50 to move down, and the first sealing ring 305 is pushed open by the first convex ribs, so that the first compression space 10 communicates with the connector inner cavity 602 through the first exhaust channel, that is, the first compression space 10 communicates with the main liquid suction cavity 301 through the first exhaust channel, and then the first compression space 10 communicates with the interior of the container; and at the same time, the second sealing cavity is pushed open by the second convex ribs, so that the second compression space 20 communicates with the exterior of the sterile spray pump through the second exhaust channel, then the interior of the container communicates with the outside, and the pressures inside and outside the container are balanced.

Figure 6:
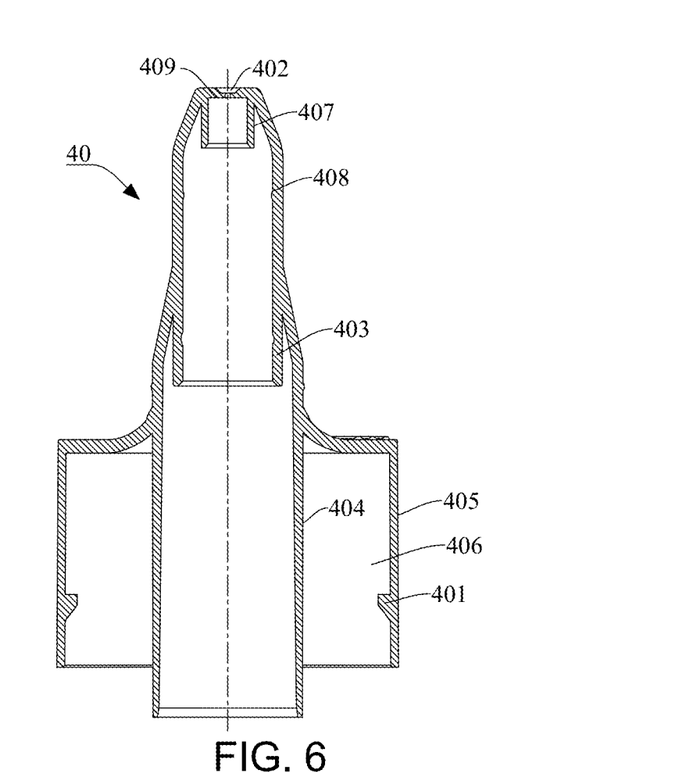
FIG. 6 is a schematic structural diagram of a spray head according to an embodiment of the present disclosure.

Further, the preferred connection structure between the main piston 30, the secondary piston 50 and the spray head 40 is as follows: as shown in FIGS. 1, 4 and 5, the secondary piston 50 includes a third connecting portion 507 bent and extending at the outer peripheral side of the secondary outer ring portion 505, and a ring of first clamping groove 508 is formed between the third connecting portion 507 and the secondary outer ring portion 505; a fourth connecting portion 403 extending downwards is provided on the inner wall of the spray head 40; and the fourth connecting portion 403 of the spray head 40 is clamped in the first clamping groove 508 of the secondary piston 50, and thus, the secondary piston 50 is fixed to the spray head 40. In addition, the main piston 30 also includes a fifth connecting portion 310, a ring of piston main body portion 311, a sixth connecting portion 312, a ring of piston connecting portion 313, the first cavity 314, and a third step portion 315, where the fifth connecting portion 310 extends horizontally and outwards from the lower end of the main outer ring portion 304; the ring of piston main body portion 311 extends upwards from the outer end of the fifth connecting portion 310; the sixth connecting portion 312 extends horizontally and outwards from the upper end of the piston main body portion 311; the ring of piston connecting portion 313 extends downwards from the outer end of the sixth connecting portion 312; the first cavity 314 is formed between the main outer ring portion 304 and the piston main body portion 311; the third step portion 315 is fixedly provided at the bottom of the first cavity 314; a first return spring 120 sleeved on the outer peripheries of the main outer ring portion 304 and the secondary outer ring portion 505 are provided in the first cavity 314; the upper and lower ends of the first return spring 120 respectively abut against the third connecting portion 507 of the secondary piston 50 and the third step portion 315 of the main piston 30; when the spray head 40 is pressed down, the first return spring 120 is compressed; after the spray head 40 is released, the secondary piston 50 and the spray head 40 rebound upwards together under the action of the first return spring 120. As shown in FIGS. 1, 4, and 6, the lower section portion of the spray head 40 includes a spray head inner ring portion 404, a spray head outer ring portion 405 located at the outer peripheral side of the spray head inner ring portion 404, and a second cavity 406 formed between the spray head inner ring portion 404 and the spray head outer ring portion 405, where the spray head inner ring portion 404 is located at the inner peripheral side of a piston main body portion 311, the spray head outer ring portion 405 is located at the outer peripheral side of the piston connecting portion 313, and therefore, the piston main body portion 311, the sixth connecting portion 312 and the piston connecting portion 313 in the main piston 30 are located in the second cavity 406 of the spray head 40. Particularly, an air channel 130 is formed by an area between the spray head inner ring portion 404 and the main outer ring portion 304, a gap between the spray head inner ring portion 404 and the piston main body portion 311, a portion of the second cavity 406 located above the sixth connecting portion 312 in the spray head 40, and a gap between the spray head outer ring portion 405 and the piston connecting portion 313, and therefore, the air channel 130 is formed between the main piston 30 and the spray head 40. The main piston 30 is provided with a ring of upper clamping portion 307 protruding outwards in a radial direction on the outer periphery of the upper end of the piston connecting portion 313. The spray head 40 is provided with a ring of lower clamping portion 401 protruding inwards in a radial direction on the inner peripheral surface of the spray head outer ring portion 405. The lower clamping portion 401 is located below the upper clamping portion 307. When the spray head 40 is not pressed down, the upper clamping portion 307 abuts against the lower clamping portion 401, the space between the lower clamping portion 401 and the piston connecting portion 313 is sealed, then the space between the spray head 40 and the main piston 30 is sealed, thus, the outside is blocked from one end of the air channel 130, and the other end of the air channel 130 is also blocked from the second compression space 20 by the second exhaust member 503; when the spray head 40 is pressed down to the lowest end, the upper clamping portion 307 is separated from the lower clamping portion 401, and the seal between the lower clamping portion 401 and the piston connecting portion 313 is released, so that one end of the air channel 130 communicates with the outside, the other end of the air channel 130 also communicates with the second compression space 20 through the second exhaust member 503, and thus, the pressures inside and outside the container are balanced.

As shown in FIGS. 1 to 3, the sterile spray pump further includes a spray nozzle 70 fixed in the spray head 40, a sealing valve 80 mounted between the spray nozzle 70 and the secondary piston 50 in a vertically movable manner, and a one-way valve assembly 90 disposed at the upper end of the secondary liquid suction cavity 501; the upper end of the spray head 40 includes a spray port 402; a spray channel 140 is formed between the secondary piston 50, the spray head 40, the sealing valve 80 and the spray nozzle 70; the one-way valve assembly 90 communicates the lower end of the spray channel 140 with the secondary liquid suction cavity 501 or blocks the lower end of the spray channel 140 from the secondary liquid suction cavity 501. After the spray head 40 is pressed down for many times and liquid in the container is sucked by the liquid suction tube 110, the connector inner cavity 602 and the secondary liquid suction cavity 501 are gradually filled with the liquid. When the secondary liquid suction cavity 501 is not filled with liquid, the one-way valve assembly 90 is in a closed state to block the spray channel 140 from the secondary liquid suction cavity 501. When the secondary liquid suction cavity 501 is filled with liquid, the pressure of the liquid forces the one-way valve assembly 90 to open to communicate the spray channel 140 with the secondary liquid suction cavity 501, so that the spray channel 140 is gradually filled with the liquid. When the spray channel 140 is not filled with liquid, the space between the spray nozzle 70, the spray head 40 and the sealing valve 80 is sealed to block the upper end of the spray channel 140 and the spray port 402. When the spray channel 140 is filled with liquid, the pressure of the liquid forces the sealing valve 80 to move downwards, so that the upper end of the spray channel 140 communicates with the spray port 402, and the liquid produces an atomizing effect after passing through the spray nozzle 70, and is sprayed out from the spray port 402 on the spray head 40; after the liquid is sprayed out, the internal pressure disappears, and the space between the spray nozzle 70, the spray head 40 and the sealing valve 80 is sealed again; the processes are repeated, and thus, residual medicinal liquid can be prevented from contacting with the air to avoid polluting air.

Further, as shown in FIG. 5, the one-way valve assembly 90 includes a valve port 901 provided on the secondary inner ring portion 504 of the secondary piston 50, a valve seat sealing surface 902 provided at the inner side of the valve port 901 and on the secondary inner ring portion 504 of the secondary piston 50, and a valve core 903 mounted in the secondary piston 50 in a vertically movable manner; the valve seat sealing surface 902 is a conical surface with the inner end obliquely extending inwards and downwards, and the valve core 903 is a stainless steel ball; the valve port 901 communicates with the lower end of the spray channel 140; when the secondary liquid suction cavity 501 is not filled with liquid, the valve core 903 is in sealing connection with the valve seat sealing surface 902, and therefore, the valve core 903 blocks the valve port 901 and the secondary liquid suction cavity 501 so as to block the spray channel 140 and the secondary liquid suction cavity 501; and when the secondary liquid suction cavity 501 is filled with liquid, the pressure of the liquid forces the valve core 903 to move upwards, so that the valve port 901 communicates with the secondary liquid suction cavity 501, and thus, the spray channel 140 communicates with the secondary liquid suction cavity 501.

Figure 7:
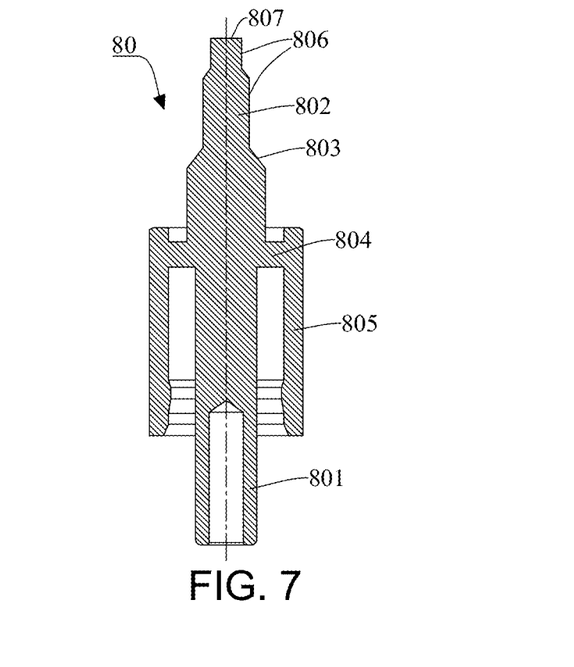
FIG. 7 is a schematic structural diagram of a sealing valve according to an embodiment of the present disclosure.

Further, as shown in FIGS. 1, 5, and 7, the sealing valve 80 includes a lower valve section portion 801 extending into the secondary piston 50, an upper valve section portion 802 extending into the spray nozzle 70, a valve connecting portion 804 extending horizontally and outwards from the joint between the lower valve section portion 801 and the upper valve section portion 802, and a valve outer ring portion 805 extending downwards from the outer end of the valve connecting portion 804 and located at the outer periphery of the lower valve section portion 801. The upper end of the secondary inner ring portion 504 in the secondary piston 50 extends between the valve outer ring portion 805 and the lower valve section portion 801. Meanwhile, the secondary piston 50 includes a fourth step portion 509 on the inner periphery of the secondary inner ring portion 504, a second return spring 150 located at the inner peripheral side of the secondary inner ring portion 504 is sleeved on the outer periphery of the lower valve section portion 801, and the upper and lower ends of the second return spring 150 respectively abut against the valve connecting portion 804 in the sealing valve 80 and the fourth step portion 509 in the secondary piston 50. When the spray channel 140 is not filled with liquid, the sealing valve 80 abuts upwards against the spray nozzle 70 and the spray head 40 under the action of the second return spring 150, so that the space between the spray nozzle 70, the spray head 40 and the sealing valve 80 is sealed. When the spray channel 140 is filled with liquid, the pressure of the liquid overcomes the applied force of the second return spring 150, and then can force the sealing valve 80 to move downwards. When the internal pressure disappears after the liquid is sprayed out, the second return spring 150 also makes the sealing valve 80 move up to abut against the spray nozzle 70 and the spray head 40. In addition, in order to facilitate the liquid to push the sealing valve 80 downwards, a section of pushing surface 803 located below the sealing joint between the sealing valve 80 and the spray nozzle 70 is provided on the outer peripheral surface of the upper valve section portion 802 of the sealing valve 80; and the pushing surface 803 is a conical surface with the outer end obliquely extending outwards and downwards.

Figure 8:
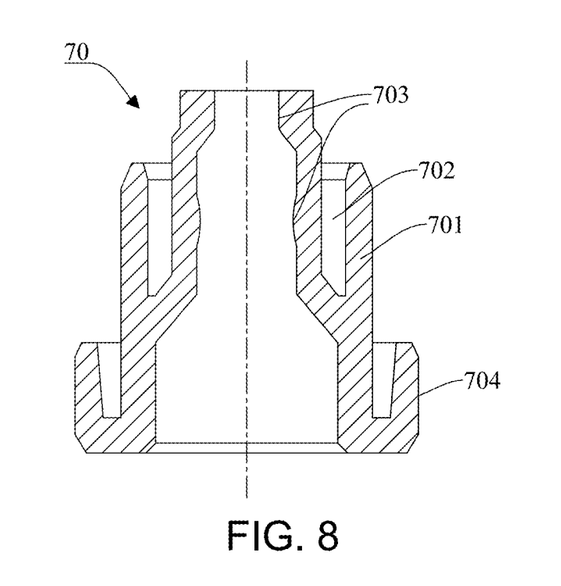
FIG. 8 is a schematic structural diagram of a spray nozzle according to an embodiment of the present disclosure.

Further, the preferred connection structure between the spray head 40 and the spray nozzle 70 is as follows: as shown in FIGS. 1, 6, and 8, a seventh connecting portion 407 extending downwards is provided on the inner wall of the upper end of the spray head 40, an eighth connecting portion 701 which is bent and extended is provided on the outer periphery of the spray nozzle 70, and a ring of second clamping groove 702 is formed between the eighth connecting portion 701 and the spray nozzle 70, the seventh connecting portion 407 of the spray head 40 is clamped in the second clamping groove 702 of the spray nozzle 70, and then the spray nozzle 70 is fixed to the spray head 40. In addition, when the spray channel 140 is not filled with liquid, the sealing structure between the spray nozzle 70, the spray head 40, and the sealing valve 80 is preferably as follows: the sealing valve 80 includes a first sealing surface 806 on the outer periphery of the upper valve section portion 802, the inner periphery of the spray nozzle 70 is provided with a second sealing surface 703, and the first sealing surface 806 fits with the second sealing surface 703 to form a circumferential seal between the upper valve section portion 802 of the sealing valve 80 and the spray nozzle 70; the outer periphery of the spray nozzle 70 is provided with a third sealing surface 704, the inner periphery of the spray head 40 is provided with a fourth sealing surface 408, and the third sealing surface 704 fits with the fourth sealing surface 408 to form a circumferential seal between the spray nozzle 70 and the spray head 40; the upper end surface of the upper valve section portion 802 of the sealing valve 80 is provided with a fifth sealing surface 807, the lower end surface of the top of the spray head 40 is provided with a sixth sealing surface 409, and the fifth sealing surface 807 fits with the sixth sealing surface 409 to form an end-face seal between the spray head 40 and the sealing valve 80. When the spray channel 140 is filled with liquid to move the sealing valve 80 down, the circumferential seal between the sealing valve 80 and the spray nozzle 70 and the end-face seal between the sealing valve 80 and the spray head 40 are released. An area between the secondary inner ring portion 504 and the upper section of the secondary outer ring portion 505, a gap between the valve outer ring portion 805 and the spray head 40, and a gap between the valve outer ring portion 805 and the spray nozzle 70 are sequentially communicated to form the spray channel 140, and the upper end of the spray channel 140 extends to the spray port 402.

In summary, the working principle of the sterile spray pump is as follows:

1. In the initial state, as shown in FIG. 1, when the spray head 40 is not pressed down, there is air in the first compression space 10 and the second compression space 20, the liquid in the container is not sucked into the connector inner cavity 602 (i.e. the main liquid suction cavity 301), the space between the main piston 30 and the secondary piston 50 is sealed, the space between the main piston 30 and the spray head 40 is sealed, the one-way valve assembly 90 in the secondary piston 50 is closed, the sealing valve 80 is circumferentially sealed to the spray nozzle 70, the sealing valve 80 is end-face sealed to the spray head 40, the space between the first compression space 10 and the connector inner cavity 602 is blocked by the first sealing ring 305, the space between the second compression space 20 and the air channel 130 is blocked by the second sealing ring 306, the space between the air channel 130 and the outside is blocked by the sealing structure between the main piston 30 and the spray head 40, therefore, when the sterile spray pump does not work, the sterile spray pump is fully sealed, and the purpose of sterility is achieved.

2. When the spray head 40 is pressed down to the lowest end for the first time, as shown in FIG. 2, the spray head 40 drives the spray nozzle 70 and the secondary piston 50 to move down together, so that the first compression space 10 and the second compression space 20 are compressed, the first return spring 120 is compressed, and the seal between the spray head 40 and the main piston 30 is released; after the first sealing ring 305 is pushed open by the first convex ribs, the compressed air in the first compression space 10 is discharged into the container through the first exhaust channel and the connector inner cavity 602; at the same time, after the second sealing cavity is pushed open by the second convex ribs, the pressures inside and outside the container are balanced, so the compressed air in the container is discharged into the exterior of the sterile spray pump after passing through the connector inner cavity 602, the air supply port 302, the second compression space 20, the second exhaust channel and the air channel 130 in sequence.

3. After the spray head 40 is released, the secondary piston 50 moves up under the action of the first return spring 120, and then the spray head 40 and the spray nozzle 70 are driven to move up and rebound together. As shown in FIG. 3, negative pressure is formed in the first compression space 10, the second compression space 20 and the connector inner cavity 602, and the liquid in the container is sucked out through the liquid suction tube 110.

4. After the spray head 40 is pressed down to the lowest end for the second time and the spray head 40 is pressed down to the lowest end every subsequent time, as the liquid in the container is sucked out, negative pressure is formed in the container; the pressure in the container is balanced with the external pressure through the first exhaust member 502 and the second exhaust member 503, so the external air is supplied into the container after passing through the air channel 130, the second exhaust channel, the second compression space 20, the air supply port 302 and the connector inner cavity 602 in sequence.

5. After the spray head 40 is released again, the secondary piston 50, the spray head 40 and the spray nozzle 70 move up and rebound together, so that the liquid in the container is sucked out again; the actions of pressing the spray head 40 to the lowest end and releasing the spray head 40 are repeated, after the connector inner cavity 602 and the secondary liquid suction cavity 501 are filled with liquid, the valve core 903 of the one-way valve assembly 90 is pushed open, and the one-way valve assembly 90 is opened; then the sealing valve 80 moves down after the spray channel 140 is filled with liquid, and the liquid produces an atomizing effect after passing through the spray nozzle 70 and is sprayed out from the spray port 402 on the spray head 40; after the liquid is sprayed out, the internal pressure disappears, the space between the spray nozzle 70, the spray head 40 and the sealing valve 80 is sealed again, and the processes are repeated.

To sum up, in the present application, the normal operation of the sterile spray pump is realized through the first compression space 10, the second compression space 20, the first exhaust member 502, the second exhaust member 503 and the air supply port 302, so that the sterile spray pump can suck the liquid in the container and spray out the liquid. As the sterile spray pump can normally supply external air into the container instead of using a vacuum pump, the sterile spray pump in the present application is not affected by the loading capacity and the number of times of use, and the capacity of the container, the loading capacity of medicinal liquid in the container and the spray dose of the spray pump are not limited, and the utilization rate of the loading capacity of the capacitor is increased. Moreover, the air exchange for the normal operation of the sterile spray pump is met through the filter element 601, the pollution is also avoided, and thus the sterile requirement is achieved.

Therefore, the present disclosure effectively overcomes various disadvantages in the prior art and has a high industrial utilization value.

The above embodiments merely illustrate the principles and effects of the present disclosure, and are not intended to limit the present disclosure. Those skilled in the art can modify or change the above embodiments without departing from the spirit and scope of the present disclosure. Therefore, all equivalent modifications or changes made by those skilled in the art without departing from the spirit and technical idea of the present disclosure should be covered by the claims of the present disclosure.

What is claimed is:

1. A sterile spray pump, comprising a main piston (30) configured to be connected to a container, a spray head (40) mounted in a vertically movable manner on the main piston (30), and a secondary piston (50) fixed inside the spray head (40), wherein the secondary piston (50) is mounted in a vertically movable manner on the main piston (30), and a first compression space (10) and a second compression space (20) are formed between the secondary piston (50) and the main piston (30); a main liquid suction cavity (301) communicating with the inner cavity of the container and an air supply port (302) communicating with the main liquid suction cavity (301) are provided in the main piston (30); the air supply port (302) communicates with the second compression space (20), and a filter element (601) covering the air supply port (302) is fixedly provided in the air supply port (302); the secondary piston (50) includes a secondary liquid suction cavity (501) communicating with the main liquid suction cavity (301), a first exhaust member (502), and a second exhaust member (503); when the spray head (40) is not pressed down, a space between the main piston (30) and the secondary piston (50) is sealed; after the spray head (40) is pressed down and the main piston (30) abuts against the first exhaust member (502) and the second exhaust member (503), the first compression space (10) communicates with the main liquid suction cavity (301) through the first exhaust member (502), and the second compression space (20) communicates with the exterior of the sterile spray pump through the second exhaust member (503).

2. The sterile spray pump as in claim 1, wherein a filter connector (60) provided in the main liquid suction cavity (301) is fixed in the main piston (30); wherein the air supply port (302) is provided in the filter connector (60); wherein the filter element (601) is a filter membrane fixed to the filter connector (60).

3. The sterile spray pump as in claim 1, wherein the main piston (30) includes a main inner ring portion (303) and a main outer ring portion (304) located at an outer peripheral side of the main inner ring portion (303); the secondary piston (50) includes a secondary inner ring portion (504) and a secondary outer ring portion (505) located at an outer peripheral side of the secondary inner ring portion (504); an upper end of the main inner ring portion (303) extends between the secondary outer ring portion (505) and the secondary inner ring portion (504), and the first compression space (10) is formed between the main inner ring portion (303), the secondary outer ring portion (505) and the secondary inner ring portion (504); and a lower end of the secondary outer ring portion (505) extends between the main inner ring portion (303) and the main outer ring portion (304), and the second compression space (20) is formed between the secondary outer ring portion (505), the main inner ring portion (303) and the main outer ring portion (304).

4. The sterile spray pump as in claim 3, wherein the main piston (30) includes a first sealing ring (305) at the upper end of the main inner ring portion (303) and a second sealing ring (306) at an upper end of the main outer ring portion (304), the first sealing ring (305) is in sealing connection with an outer peripheral surface of the secondary inner ring portion (504), and the second sealing ring (306) is in sealing connection with an outer peripheral surface of the secondary outer ring portion (505); the first exhaust member (502) comprises at least two first convex ribs fixedly provided on the outer peripheral surface of the secondary inner ring portion (504) and arranged in a circumferential direction of the secondary inner ring portion (504), and a first exhaust channel formed between two adjacent first convex ribs; the second exhaust member (503) comprises at least two second convex ribs fixedly provided on the outer peripheral surface of the secondary outer ring portion (505) and arranged in a circumferential direction of the secondary outer ring portion (505), and a second exhaust channel formed between two adjacent second convex ribs; and after the spray head (40) is pressed down, the first convex ribs push the first sealing ring (305) open to make the first compression space (10) communicate with the main liquid suction cavity (301) through the first exhaust channel, and the second convex ribs push the second sealing ring (306) to make the second compression space (20) communicate with the exterior of the sterile spray pump through the second exhaust channel.

5. The sterile spray pump as in claim 3, further comprising a first return spring (120) sleeved on outer peripheries of the main outer ring portion (304) and the secondary outer ring portion (505), wherein upper and lower ends of the first return spring (120) respectively abut against the secondary piston (50) and the main piston (30).

6. The sterile spray pump as in claim 1, wherein an air channel (130) is formed between the main piston (30) and the spray head (40), an outer periphery of the main piston (30) is provided with a ring of upper clamping portion (307) protruding outwards in a radial direction, and an inner periphery of the spray head (40) is provided with a ring of lower clamping portion (401) protruding inwards in a radial direction; when the spray head (40) is not pressed down, the upper clamping portion (307) abuts against the lower clamping portion (401), and a space between the lower clamping portion (401) and the main piston (30) is sealed; after the spray head (40) is pressed down, the upper clamping portion (307) is separated from the lower clamping portion (401), and the seal between the lower clamping portion (401) and the main piston (30) is released; and one end of the air channel (130) communicates with the exterior of the sterile spray pump, and the other end of the air channel (130) communicates with the second compression space (20) through the second exhaust member (503).

7. The sterile spray pump as in claim 1, further comprising a spray nozzle (70) fixed in the spray head (40), a sealing valve (80) mounted between the spray nozzle (70) and the secondary piston (50) in a vertically movable manner, and a one-way valve assembly (90) disposed at an upper end of the secondary liquid suction cavity (501); wherein the spray head (40) includes a spray port (402), a spray channel (140) is formed between the secondary piston (50), the spray head (40), the sealing valve (80) and the spray nozzle (70), and the one-way valve assembly (90) is configured to communicate the spray channel (140) with the secondary liquid suction cavity (501) or block the spray channel (140) from the secondary liquid suction cavity (501); when the spray channel (140) is not filled with liquid, a space between the spray nozzle (70), the spray head (40) and the sealing valve (80) is sealed to block the spray channel (140) from the spray port (402); and when the spray channel (140) is filled with liquid, the sealing valve (80) moves downward to make the spray channel (140) communicate with the spray port (402).

8. The sterile spray pump as in claim 7, wherein the sealing valve (80) comprises a lower valve section portion (801) extending into the secondary piston (50), wherein a second return spring (150) is sleeved on an outer periphery of the lower valve section portion (801), wherein upper and lower ends of the second return spring (150) respectively abut against the sealing valve (80) and the secondary piston (50).

9. The sterile spray pump as in claim 7, wherein the sealing valve (80) comprises an upper valve section portion (802) extending into the spray nozzle (70); wherein when the spray channel (140) is not filled with liquid, a the upper valve section portion (802) is circumferentially sealed to the spray nozzle (70), the spray nozzle (70) is circumferentially sealed to the spray head (40), and the spray head (40) is end-face sealed to the sealing valve (80).

10. The sterile spray pump as in claim 7, wherein the sealing valve (80) includes a section of pushing surface (803) located below a sealing joint of the sealing valve (80) and the spray nozzle (70), wherein the pushing surface (803) is a conical surface with an outer end obliquely extending outwards and downwards.

11. The sterile spray pump as in claim 7, wherein the one-way valve assembly (90) comprises a valve port (901) opened on the secondary piston (50), a valve seat sealing surface (902) provided at an inner side of the valve port (901) and on the secondary piston (50), and a valve core (903) mounted in the secondary piston (50) in a vertically movable manner, wherein the valve port (901) communicates with the spray channel (140); wherein when the secondary liquid suction cavity (501) is not filled with liquid, the valve core (903) is in sealing connection with the valve seat sealing surface (902), and the valve core (903) blocks the valve port (901) from the secondary liquid suction cavity (501); wherein when the secondary liquid suction cavity (501) is filled with liquid, the valve core (903) moves upwards, and the valve port (901) communicates with the secondary liquid suction cavity (501).

12. The sterile spray pump as in claim 11, wherein the valve seat sealing surface (902) is a conical surface with an inner end obliquely extending inwards and downwards, and the valve core (903) is a stainless steel ball.

\* \* \* \* \*